United States Patent
Puls et al.

(10) Patent No.: US 10,045,932 B2
(45) Date of Patent: Aug. 14, 2018

(54) AGENTS AND METHOD FOR THE TEMPORARY SHAPING OF KERATIN-CONTAINING FIBERS

(71) Applicant: Henkel AG & Co. KGaA, Duesseldorf (DE)

(72) Inventors: Anna Puls, Winsen (DE); Sandra Fuchs, Pinneberg (DE); Nora Koopmann, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/352,700

(22) Filed: Nov. 16, 2016

(65) Prior Publication Data

US 2017/0143615 A1   May 25, 2017

(30) Foreign Application Priority Data

Nov. 25, 2015 (DE) .......................... 10 2015 223 349

(51) Int. Cl.
| | |
|---|---|
| *A61K 8/25* | (2006.01) |
| *A61K 8/92* | (2006.01) |
| *A61K 8/26* | (2006.01) |
| *A61K 8/27* | (2006.01) |
| *A61K 8/29* | (2006.01) |
| *A61K 8/31* | (2006.01) |
| *A61K 8/73* | (2006.01) |
| *A61Q 5/06* | (2006.01) |

(52) U.S. Cl.
CPC .................. *A61K 8/92* (2013.01); *A61K 8/25* (2013.01); *A61K 8/26* (2013.01); *A61K 8/27* (2013.01); *A61K 8/29* (2013.01); *A61K 8/31* (2013.01); *A61K 8/732* (2013.01); *A61Q 5/06* (2013.01)

(58) Field of Classification Search
CPC ... A61K 8/25; A61K 8/26; A61K 8/27; A61K 8/29; A61K 8/31; A61K 8/732; A61K 8/92; A61Q 5/06
See application file for complete search history.

(56) References Cited

U.S. PATENT DOCUMENTS

| | | | |
|---|---|---|---|
| 8,021,651 B2 | 9/2011 | Hentrich et al. | |
| 2003/0145395 A1* | 8/2003 | Murakami | A61K 8/494 8/405 |
| 2007/0092471 A1* | 4/2007 | Cassier | A61K 8/66 424/70.14 |
| 2009/0185984 A1* | 7/2009 | Gutkowski | A61K 8/898 424/49 |
| 2010/0209376 A1* | 8/2010 | Richters | A61K 8/25 424/70.12 |

FOREIGN PATENT DOCUMENTS

| | | | | |
|---|---|---|---|---|
| DE | 102008057261 A1 | | 5/2010 | |
| JP | 2007070232 A | | 3/2007 | |
| WO | WO 2007073799 | * | 7/2007 | ............... A71K 8/04 |
| WO | 2009082565 A1 | | 7/2009 | |
| WO | 2013190080 A2 | | 12/2013 | |

OTHER PUBLICATIONS

Gooch, J.W. Encyclopedic Dictionary of Polymers, vol. 1, 2010 p. 572; 1 page.*
English translation of WO 2007073799 dated Jul. 2007; 7 pages.*
UKIPO Search Report GB 2551213 Completed: Sep. 27, 2017 2 pages.

* cited by examiner

*Primary Examiner* — Ernst V Arnold
(74) *Attorney, Agent, or Firm* — P. Scott Smith

(57) ABSTRACT

Cosmetic compositions including, based on their total weight,
a) 10 to 90% by weight of a hydrocarbon or hydrocarbon mixture with a melting point between 38° C. and 58° C.,
b) 1.0 to 45% by weight of a silicate from the group of phyllosilicate and aluminosilicate,
c) 0.01 to 7.0% by weight of a hydrophobized metal oxide powder,
d) 0.01 to 3.0% by weight of at least one white pigment,
e) 3.0 to 15% by weight of wax,
f) 0.5 to 15% by weight of an emulsifier, and
g) less than 3.0% by weight of water
the use thereof for the temporary shaping of keratinic fibers, and a method using these compositions.

14 Claims, No Drawings

AGENTS AND METHOD FOR THE TEMPORARY SHAPING OF KERATIN-CONTAINING FIBERS

FIELD OF THE INVENTION

The present invention generally relates to the technical field of the temporary shaping of keratin-containing fibers, in particular human hair.

BACKGROUND OF THE INVENTION

Styling agents for shaping keratin-containing fibers have been known for some time and are used in various forms for volumizing, refreshing, and retaining hairstyles, which for many hair types can only be achieved using setting active substances. Both hair treatment agents used to shape hair permanently and those that shape it temporarily play an important role in this respect.

Sprayable products as well as product forms that are worked into the hairstyle with the aid of a comb or with the fingers are suitable for the temporary shaping of keratin-containing fibers. The last-mentioned product group comprises oils as well as gels, creams, and powders. Powdered styling agents in particular are enjoying increasing popularity because of their easy dispensability and their cosmetic properties such as a high hairstyle hold, increase in volume, remodellability, and their matting effect.

German patent application DE 102008057261 A1 therefore describes powdered compositions which are used for the temporary reshaping of hair for a very strong hold of the set hairstyle.

The subject of the international application WO 2007/051511 A1 is the use of a powdered composition, including 50 to 95% by weight of an aqueous solvent, hydrophobized silicon dioxide powder, and a film-forming and/or setting polymer, present at least in the aqueous solvent, for the temporary shaping of keratinic fibers.

The powdered hair cosmetics of the state of the art meanwhile do in fact provide a good hold and high volume, and are notable for good dispensability. The matting effect associated with the use of these agents, however, does not satisfy the wish of all consumers and is replaced, at least partially, by the wish for hair care and hair shine.

The object of the present invention, therefore, was to provide hair treatment agents for the temporary shaping, which are notable for an increased hair shine, apart from a good hairstyle hold, high hair volume, and remodellability. The agents should be usable, moreover, on wet and on dry hair.

It was established that these objects can be achieved with the aid of a complex active substance mixture, to which, apart from other components, inter alia, a hydrophobized metal oxide powder, usually used in powdered styling agents, is added.

Furthermore, other desirable features and characteristics of the present invention will become apparent from the subsequent detailed description of the invention and the appended claims, taken in conjunction with this background of the invention.

BRIEF SUMMARY OF THE INVENTION

A cosmetic composition including, based on its total weight, 10 to 90% by weight of hydrocarbons with a melting point between 38° C. and 58° C., 1.0 to 45% by weight of a silicate from the group of phyllosilicate and aluminosilicate, 0.01 to 7.0% by weight of a hydrophobized metal oxide powder, 0.01 to 3.0% by weight of at least one white pigment, 3.0 to 15% by weight of wax, 0.5 to 15% by weight of an emulsifier, and less than 3.0% by weight of water.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the present invention constitutes cosmetic compositions including, based on their total weight,
a) 10 to 90% by weight of a hydrocarbon or hydrocarbon mixture with a melting point between 38° C. and 58° C.,
b) 1.0 to 45% by weight of a silicate from the group of phyllosilicate and aluminosilicate,
c) 0.01 to 7.0% by weight of a hydrophobized metal oxide powder,
d) 0.01 to 3.0% by weight of at least one white pigment,
e) 3.0 to 15% by weight of wax,
f) 0.5 to 15% by weight of an emulsifier, and
g) less than 3.0% by weight of water.

The agents of the invention are preferably present in the form of creams or pastes. The drop point (Mettler Toledo FP83HT (dropping point cell), Mettler Toledo FP90 (central processor): start temperature 40° C., end temperature 70° C., heating rate 1° C./min) of the agents of the invention is preferably between 45° C. and 65° C., preferably between 50° C. and 60° C.

A first essential component of compositions of the invention are hydrocarbons or hydrocarbon mixtures capable of melting. Preferred hydrocarbons or hydrocarbon mixtures have a melting point between 45 and 58° C., preferably between 50 and 58° C. The applicability of agents of the invention is also improved by the hydrocarbon melting point, such as their hair cosmetic properties in regard to hold, volume, and remodellability.

The weight proportion of the hydrocarbon or hydrocarbon mixture in terms of the total weight of the cosmetic composition is preferably 15 to 70% by weight, preferably 20 to 50% by weight, and in particular 25 to 40% by weight.

The use of hydrocarbon mixtures is particularly preferred. Suitable mixtures can comprise branched and unbranched, saturated and unsaturated hydrocarbons. Very particularly preferred is the use of hydrocarbon mixtures with the INCI name Petrolatum, as are marketed, for example, under the trade name "Weichceresin® FL 400" (a vaseline/vaseline oil/wax mixture with a melting point of 50-54° C.; manufacturer: Parafluid Mineralölgesellschaft).

The second essential component of the cosmetic compositions of the invention is the silicate from the group of phyllosilicate and aluminosilicate.

The weight proportion of silicate b) in terms of the total weight of the cosmetic composition is preferably 10 to 45% by weight, preferably 20 to 45% by weight, and in particular 25 to 40% by weight.

Phyllosilicate or aluminosilicate but mixtures of both silicates as well can be used. The use of kaolin is particularly preferred.

A further essential component of the compositions of the invention is the hydrophobized metal oxide powder. Preferred compositions are characterized in that they include the hydrophobized metal oxide powder, based on their total weight, in amounts of 0.02 to 6.0% by weight, preferably 0.05 to 5.0% by weight, and in particular 0.1 to 5.0% by weight. The optimal amount in this case depends, in addition to the weight proportions of the other components, primarily on the hydrophobicity of the employed silicon dioxide powder.

Metal oxides that have been modified, at least on the surface of the particles such that the modified particle is wetted less by water than the unmodified particle, are to be understood as hydrophobized in the context of the invention.

The particle diameter of the primary particles of preferred hydrophobized metal oxides is preferably less than 5 μm, particularly preferably less than 1 μm, and in particular between 1 and 50 nm.

At least one representative of the group formed by silanes, halosilanes, alkoxysilanes, and silazanes is preferably suitable according to the invention as a reagent for silanizing the metal oxide. Preferably suitable hydrophobized metal oxides of the hydrophobized metal oxide powder are selected according to the invention from at least one representative of the group formed by hydrophobized silicates, hydrophobized aluminosilicates, hydrophobized titanium dioxide, and hydrophobized silicon dioxide. Hydrophobized silicates have proven to be particularly suitable for preparing the cosmetic compositions of the invention, pyrogenic silicic acid aftertreated by silanization or by reaction with polydimethylsiloxane having particular advantages.

Particularly preferably, the powdered composition of the invention includes as the hydrophobized metal oxide powder at least hydrophobized silicon dioxide. Preferred furthermore are hydrophobized silicon dioxides that have a specific BET surface between 10 and 400 m$^2$/g, preferably between 40 to 300 m$^2$/g, and in particular 80 to 150 m$^2$/g.

Particularly preferably, the powdered composition of the invention includes as the hydrophobized metal oxide powder at least silanized, hydrophobized silicon dioxide. Preferably, at least one representative of the group formed by silanes, halosilanes, alkoxysilanes, and silazanes is suitable according to the invention as a reagent for silanizing the silicon dioxide.

Preferred representatives of the group of silanes are hexa(C$_1$-C$_{20}$) alkyl disilanes, particularly hexamethyldisilane.

If a halosilane is used as the silylating agent, selected as the preferred halosilane is at least one compound from the group formed by the compounds

[(C$_1$-C$_{20}$)alkyl]$_z$SiX$_{(4-z')}$

X$_3$Si[(CH$_2$)$_n$—R]

X$_2$[(C$_1$-C$_{20}$)alkyl]Si(CH$_2$)$_n$—R

[(C$_1$-C$_{20}$)alkyl]$_{(y'+1)}$[R—(CH$_2$)$_n$]$_{(2-y')}$SiX, where
X denotes a chlorine, bromine, or iodine atom,
z' is a number 1, 2, or 3,
y' is a number 0, 1, or 2,
n is an integer from 1 to 20, and
R stands for a group from
(C$_1$-C$_{10}$)alkyl-, aryl-, (C$_1$-C$_6$)perfluoroalkyl-, —NH$_2$, —N$_3$, —SCN, —CH=CH$_2$, —O(O)C—C(CH$_3$)=CH$_2$, —OCH$_2$—CH=CH$_2$,

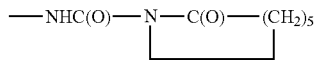

—NH—C(O)O-Me, —NH—C(O)O-Et, —NH—(CH$_2$)$_3$—Si(O(C$_1$-C$_6$)alkyl)$_3$.

If an alkoxysilane is used as the silylating agent, selected as the preferred alkoxysilane is at least one compound from the group formed by the compounds

[(C$_1$-C$_{20}$)alkylO]$_z$Si(C$_1$-C$_{20}$)alkyl$_{(4-z)}$

[(C$_1$-C$_{20}$)alkylO]$_z$Si[(CH$_2$)$_n$—R]$_{(4-z)}$

[(C$_1$-C$_{20}$)alkylO]$_2$[(C$_1$-C$_{20}$)alkyl]Si(CH$_2$)$_n$—R

[(C$_1$-C$_{20}$)alkylO][(C$_1$-C$_{20}$)alkyl]2Si(CH$_2$)$_n$—R

[(C$_1$-C$_{20}$)alkylO][(C$_1$-C$_{20}$)alkyl]Si[(CH$_2$)$_n$—R]$_2$ (C$_1$-C$_{20}$alkyl)$_3$SiO—C(CH$_3$)=N—Si(C$_1$-C$_{20}$)alkyl$_3$, where
n is an integer from 1 to 20, and
z denotes a number 1, 2, or 3,
R stands for a group from
(C$_1$-C$_{20}$)alkyl-, aryl-, (C$_1$-C$_6$)perfluoroalkyl-, —NH$_2$, —N$_3$, —SCN, —CH=CH$_2$, —O(O)C—C(CH$_3$)=CH$_2$, —OCH$_2$—CH=CH$_2$,

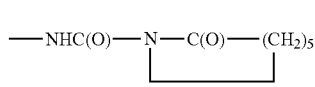

—NH—C(O)O-Me, —NH—C(O)O-Et, —NH—(CH$_2$)$_3$—Si(O(C$_1$-C$_6$)alkyl)$_3$.

Selected as the preferred silazane is at least one compound from the class of disilazanes, in particular at least one compound from disilazanes of the formula R'$_2$R"Si—NH—SiR'$_2$R"

where
R' denotes a (C$_1$-C$_{20}$) alkyl group and
R" denotes a (C$_1$-C$_{20}$) alkyl group or a vinyl group. A particularly preferred silazane is hexamethyldisilazane.

All of the aforesaid alkyl groups, whether (C$_1$-C$_6$) alkyl, (C$_1$-C$_{10}$) alkyl, or (C$_1$-C$_{20}$) alkyl, can be both cyclic and linear or branched. Examples of alkyl groups usable according to the invention are methyl, ethyl, n-propyl, isopropyl, n-butyl, cyclopentyl, cyclohexyl, n-decyl, lauryl, myristyl, cetyl, stearyl, isostearyl, and behenyl.

An example of an aryl group of the invention is the phenyl group.

Examples of a (C$_1$-C$_6$) perfluoroalkyl group of the invention are trifluoromethyl, perfluoroethyl, perfluoropropyl, and perfluorohexyl.

Used preferably are hydrophobized silicon dioxides obtained by silanization of pyrogenic silicon dioxide.

Silanized, hydrophobized silicon dioxides are selected particularly preferably from at least one compound of the group formed by trimethyl silylate-coated silicon dioxide, dimethyl silylate-coated silicon dioxide, and octyl silylate-coated silicon dioxide.

Used preferably are hydrophobized silicon dioxides obtained by silanization of pyrogenic silicon dioxide. Compositions that include as the hydrophobized metal oxide powder a hydrophobized silicate obtained by silanization of pyrogenic silicon dioxide are preferred because of their product properties, in particular their storage stability and their cosmetic action.

A variety of suitable hydrophobized silicon dioxides are commercially available. Recited as examples are Aerosil® R104 V, Aerosil® R106, Aerosil® R202, Aerosil® R805, Aerosil® R812, Aerosil® R812S, Aerosil® R972, and Aerosil® R8200, all from Degussa, and HDK® H2000, HDK® H2050, and HDK® H3004, all from Wacker.

It is particularly preferred to use hydrophobized silicon dioxides that are obtainable under the names Aerosil® R202, Aerosil® R812S, or Aerosil® R972. It is very particularly preferred to use the silicon dioxide with the INCI name Silica Silylate, which is marketed by the company Degussa under the name Aerosil® R812S.

Aftertreatment with polydimethylsiloxane offers an alternative to the hydrophobizing by silanization. Suitable compositions of the invention are those that include pyrogenic silicic acid aftertreated with polydimethylsiloxane. Suitable metal oxides with the INCI name "Silica Dimethicone Silylate" are marketed, for example, by the company Evonik under the trade name Aerosil® 8202.

A fourth essential component of the cosmetic compositions of the invention is white pigment d). White pigments are achromatic inorganic pigments with a high refractive index (preferably greater than 1.8), which are usually produced synthetically and are used primarily for creating optical whiteness in coating compositions or as fillers in, e.g., plastics. Titanium dioxide primarily can be used particularly preferably according to the invention; in addition, zinc oxide, zinc sulfide, lithopone, and aluminum starch octenylsuccinate, rather uncommon for the technical purposes, has proven suitable according to the invention.

The weight proportion of the white pigment in terms of the total weight of the cosmetic compositions is preferably 0.02 to 2.0% by weight, preferably 0.05 to 1.5% by weight, and in particular 0.1 to 1.0% by weight.

The degree of hold of the temporarily shaped keratinic fibers is increased by the addition of the white pigment. The shine of the hair is reduced. Moreover, the texture and feel of the hair are improved.

The compositions of the invention include a wax e) as the fifth essential component. This wax is different from the hydrocarbons and hydrocarbon mixtures according to feature a). The amount of the wax employed, based on the total weight of the compositions, is preferably 4.5 to 13.5% by weight, preferably 6.0 to 12% by weight, and in particular 7.0 to 11% by weight.

Preferred waxes have a melting point in the range of 40° C. to 90° C., particularly preferably in the range of 50° C. to 85° C., and in particular in the range of 50° C. to 75° C.

All waxes can be used in principle that melt in the mentioned temperature range and are physiologically compatible. Waxes particularly preferred according to the invention are beeswax, carnauba wax, candelilla wax, montan wax, and microcrystalline waxes, but preferably beeswax.

It was possible to achieve an unexpected increase in volume of the temporarily shaped keratinic fibers by the addition of wax to the cosmetic preparations used according to the invention.

A further essential component of the cosmetic preparations is lastly emulsifier f). It has proven advantageous for the storage stability, applicability, and cosmetic properties of the compositions of the invention, if said compositions, based on their total weight, include 1.0 to 14% by weight, preferably 1.5 to 12% by weight, and in particular 2.0 to 10% by weight of emulsifier.

Anionic emulsifiers form a first group of particularly preferred emulsifiers f). The anionic emulsifiers are preferably selected from the group of phosphorylated, in particular phosphorylated alkoxylated emulsifiers, particularly preferably from the group of alkyl and/or alkenyl ether phosphates. Phosphoric acid mono-, di-, or triesters of alkoxylated C12/C14 fatty alcohols in particular are particularly preferred. Examples of emulsifiers of this kind are the compounds with the INCI name Trilaureth-4-Phosphate, which are marketed, for example, by the company Clariant under the trade name Hostaphat® KL 340.

Nonionic emulsifiers form a further group of preferred emulsifiers f). Preferred in particular are nonionic emulsifiers from the group of ethoxylated unsaturated fatty alcohols, preferably from the group of ethoxylated unsaturated C16-18 fatty alcohols with an average ethoxylation degree of 4 to 6. Ethoxylated fatty alcohols with the INCI names Oleth-4, Oleth-5, and Oleth-6, in particular Oleth-5, are very particularly preferred.

Preferred in particular is the use of emulsifier mixtures, preferably of mixtures of anionic and nonionic emulsifiers. The use of mixtures of phosphoric acid mono-, di-, or triesters of alkoxylated C12/C14 fatty alcohols with ethoxylated unsaturated C16-18 fatty alcohols with an average ethoxylation degree of 4 to 6 has proven especially advantageous technically.

The agents of the invention preferably include only small amounts of solvent. In particular, their low water content below 5% by weight is particularly characteristic for these agents. Preferred cosmetic compositions are characterized in that they contain, based on their total weight, less than 3.0% by weight, preferably less than 2.0% by weight, and in particular less than 1.1% by weight of water.

In addition to the previously described components a) to g), the cosmetic preparations of the invention can include further active substances, aids, or care substances; active substances or aids that improve the producibility, applicability, and/or cosmetic action of the cosmetic preparations of the invention are preferred in particular. Nevertheless, it is preferred, however, if the composition, based on its total weight, consists of at least 60% by weight, preferably at least 70% by weight, and in particular at least 80% by weight of components a) to g).

The agent can include as a care substance, for example, at least one protein hydrolysate and/or a derivative thereof. Protein hydrolysates are product mixtures obtained by acid-, base-, or enzyme-catalyzed degradation of proteins. The term 'protein hydrolysates' according to the invention is also understood to be total hydrolysates, as well as individual amino acids and derivatives thereof, and mixtures of different amino acids. The molar weight of protein hydrolysates usable according to the invention is between 75 (the molar weight of glycine) and 200,000; the molar weight is preferably 75 to 50,000 daltons, and very particularly preferably 75 to 20,000 daltons.

The agent according to the invention can include further at least one vitamin, provitamin, vitamin precursor, and/or a derivative thereof as a care substance. The vitamins, provitamins, and vitamin precursors that are usually assigned to the groups A, B, C, E, F, and H are preferred according to the invention.

Other care substances are panthenol, caffeine, nicotinamide, and sorbitol.

The agents of the invention, furthermore, can include at least one plant extract but also mono- or oligosaccharides and/or lipids as a care substance.

The composition of some preferred cosmetic agents can be obtained from the following tables (data are given in percentages by weight, based on the total weight of the cosmetic agent, unless otherwise stated).

|  | Formula 1 | Formula 2 | Formula 3 | Formula 4 | Formula 5 |
|---|---|---|---|---|---|
| Hydrocarbon or hydrocarbon mixture* | 10 to 90 | 15 to 70 | 20 to 50 | 20 to 50 | 25 to 40 |
| Silicate from the group of phyllosillicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 6 | Formula 7 | Formula 8 | Formula 9 | Formula 10 |
|---|---|---|---|---|---|
| Petrolatum* | 10 to 90 | 15 to 70 | 20 to 50 | 20 to 50 | 25 to 40 |
| Silicate from the group of phyllosillicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 11 | Formula 12 | Formula 13 | Formula 14 | Formula 15 |
|---|---|---|---|---|---|
| Hydrocarbon or hydrocarbon mixture* | 10 to 90 | 15 to 70 | 20 to 50 | 20 to 50 | 25 to 40 |
| Kaolin | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 16 | Formula 17 | Formula 18 | Formula 19 | Formula 20 |
|---|---|---|---|---|---|
| Hydrocarbon or hydrocarbon mixture* | 10 to 90 | 15 to 70 | 20 to 50 | 20 to 50 | 25 to 40 |
| Silicate from the group of phyllosillicate and aluminosilicate | 1.0 to 45 | 10 to 45 | 20 to 45 | 20 to 45 | 25 to 40 |
| Silica silylate | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 21 | Formula 22 | Formula 23 | Formula 24 | Formula 25 |
|---|---|---|---|---|---|
| Hydrocarbon or hydrocarbon mixture* | 10 to 90 | 15 to 70 | 20 to 50 | 20 to 50 | 25 to 40 |
| Silicate from the group of phyllosilicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| Titanium dioxide | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 26 | Formula 27 | Formula 28 | Formula 29 | Formula 30 |
|---|---|---|---|---|---|
| Hydrocarbon or hydrocarbon mixture* | 10 to 90 | 15 to 70 | 20 to 50 | 20 to 50 | 25 to 40 |
| Silicate from the group of phyllosilicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Beeswax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 31 | Formula 32 | Formula 33 | Formula 34 | Formula 35 |
|---|---|---|---|---|---|
| Hydrocarbon or hydrocarbon mixture* | 10 to 90 | 15 to 70 | 20 to 50 | 20 to 50 | 25 to 40 |
| Silicate from the group of phyllosilicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Phosphoric acid mono-, di-, or triesters of alkoxylated C12/C14 fatty alcohols | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

|  | Formula 36 | Formula 37 | Formula 38 | Formula 39 | Formula 40 |
|---|---|---|---|---|---|
| Hydrocarbon or hydrocarbon mixture* | 10 to 90 | 15 to 70 | 20 to 50 | 20 to 50 | 25 to 40 |

-continued

| | Formula 36 | Formula 37 | Formula 38 | Formula 39 | Formula 40 |
|---|---|---|---|---|---|
| Silicate from the group of phyllosillicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| C16-18 fatty alcohols with an average ethoxylation degree of 4 to 6 | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

| | Formula 41 | Formula 42 | Formula 43 | Formula 44 | Formula 45 |
|---|---|---|---|---|---|
| Hydrocarbon or hydrocarbon mixture* | 10 to 90 | 15 to 70 | 20 to 50 | 20 to 50 | 25 to 40 |
| Silicate from the group of phyllosillicate and aluminosilicate | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Mixtures comprising C16-18 fatty alcohols with an ethoxylation degree of 4 to 6 and phosphoric acid mono-, di-, or triesters of alkoxylated C12/C14 fatty alcohols | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

| | Formula 46 | Formula 47 | Formula 48 | Formula 49 | Formula 50 |
|---|---|---|---|---|---|
| Petrolatum* | 10 to 90 | 15 to 70 | 20 to 50 | 20 to 50 | 25 to 40 |
| Kaolin | 1.0 to 45 | 10 to 45 | 20 to 45 | 20 to 45 | 25 to 40 |
| Silica silylate | 0.01 to 7.0 | 0.01 to 6.0 | 0.05 to 5.0 | 0.1 to 5.0 | 0.1 to 5.0 |
| Titanium dioxide | 0.01 to 3.0 | 0.02 to 2.0 | 0.05 to 1.5 | 0.05 to 1.5 | 0.1 to 1.0 |
| Wax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

| | Formula 51 | Formula 52 | Formula 53 | Formula 54 | Formula 55 |
|---|---|---|---|---|---|
| Petrolatum* | 10 to 90 | 15 to 70 | 20 to 50 | 20 to 50 | 25 to 40 |
| Kaolin | 1.0 to 45 | 10 to 45 | 20 to 45 | 20 to 45 | 25 to 40 |
| Hydrophobized metal oxide powder | 0.01 to 7.0 | 0.01 to 6.0 | 0.05 to 5.0 | 0.1 to 5.0 | 0.1 to 5.0 |
| White pigment | 0.01 to 3.0 | 0.02 to 2.0 | 0.05 to 1.5 | 0.05 to 1.5 | 0.1 to 1.0 |
| Beeswax | 3.0 to 15 | 3.0 to 15 | 4.5 to 13.5 | 6.0 to 12 | 7.0 to 11 |
| Emulsifier | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

| | Formula 56 | Formula 57 | Formula 58 | Formula 59 | Formula 60 |
|---|---|---|---|---|---|
| Petrolatum* | 10 to 90 | 15 to 70 | 20 to 50 | 20 to 50 | 25 to 40 |
| Kaolin | 1.0 to 45 | 10 to 45 | 20 to 45 | 20 to 45 | 25 to 40 |
| Silica sylilate | 0.01 to 7.0 | 0.01 to 6.0 | 0.05 to 5.0 | 0.1 to 5.0 | 0.1 to 5.0 |
| Titanium dioxide | 0.01 to 3.0 | 0.02 to 2.0 | 0.05 to 1.5 | 0.05 to 1.5 | 0.1 to 1.0 |
| Beeswax | 3.0 to 15 | 3.0 to 15 | 4.5 to 13.5 | 6.0 to 12 | 7.0 to 11 |
| Mixtures comprising C16-18 fatty alcohols with an ethoxylation degree of 4 to 6 and phosphoric acid mono-, di-, or triesters of alkoxylated C12/C14 fatty alcohols | 0.5 to 15 | 0.5 to 15 | 1.0 to 14 | 1.5 to 12 | 2.0 to 10 |
| Water | <3.0 | <3.0 | <2.5 | <2.0 | <1.1 |
| Optional additives | To 100 | To 100 | To 100 | To 100 | To 100 |

*with a melting point between 38° C. and 58° C., preferably between 45 and 58° C.

A second subject of the present invention is the use of a cosmetic composition of the invention for the temporary shaping of keratin-containing fibers, in particular human hair.

A third subject of the present invention is a method for the temporary shaping of keratin-containing fibers, in particular human hair, in which the keratinic fibers are acted upon by a cosmetic composition of the invention and are fixed temporarily in their shape.

The statements made about the cosmetic compositions of the invention apply mutatis mutandis to further preferred embodiments of the use of the invention and the method of the invention.

The compositions, uses, and methods of the invention and some of their preferred embodiments are characterized by the following points:

1. A cosmetic composition including, based on its total weight,
    a) 10 to 90% by weight of a hydrocarbon or hydrocarbon mixture with a melting point between 38° C. and 58° C.,
    b) 1.0 to 45% by weight of a silicate from the group of phyllosilicate and aluminosilicate,
    c) 0.01 to 7.0% by weight of a hydrophobized metal oxide powder,
    d) 0.01 to 3.0% by weight of at least one white pigment,
    e) 3.0 to 15% by weight of wax,
    f) 0.5 to 15% by weight of an emulsifier, and
    g) less than 3.0% by weight of water.

2. The cosmetic composition according to point 1, wherein the composition includes, based on its total weight, 15 to 70% by weight, preferably 20 to 50% by weight, and in particular 25 to 40% by weight of the hydrocarbon or hydrocarbon mixture with a melting point between 38° C. and 58° C.

3. The cosmetic composition according to one of the preceding points, wherein the melting point of the hydrocarbon or hydrocarbon mixture is between 45 and 58° C., preferably between 50 and 58° C.

4. The cosmetic composition according to one of the preceding points, wherein the composition includes, based on its total weight, 10 to 45% by weight, preferably 20 to 45% by weight, and in particular 25 to 40% by weight of a silicate from the group of phyllosilicate and aluminosilicate.

5. The cosmetic composition according to one of the preceding points, wherein the composition includes kaolin as the silicate from the group of phyllosilicate and aluminosilicate.

6. The cosmetic composition according to one of the preceding points, wherein the composition includes, based on its total weight, 0.02 to 6.0% by weight, preferably 0.05 to 5.0% by weight, and in particular 0.1 to 5.0% by weight of a hydrophobized metal oxide powder.

7. The cosmetic composition according to one of the preceding points, wherein the composition includes a hydrophobized metal oxide powder from the group of hydrophobized silicate obtained by silanization of pyrogenic silicon dioxide.

8. The cosmetic composition according to one of the preceding points, wherein the composition includes, based on its total weight, 0.02 to 2.0% by weight, preferably 0.05 to 1.5% by weight, and in particular 0.1 to 1.0% by weight of a white pigment.

9. The cosmetic composition according to one of the preceding points, wherein the white pigment is selected from the group comprising titanium oxide, zinc oxide, zinc sulfide, lithopone, and aluminum starch octenylsuccinate, preferably titanium oxide.

10. The cosmetic composition according to one of the preceding points, wherein the composition includes, based on its total weight, 4.5 to 13.5% by weight, preferably 6.0 to 12% by weight, and in particular 7.0 to 11% by weight of wax.

11. The cosmetic composition according to one of the preceding points, wherein the wax is selected from the group comprising beeswax, carnauba wax, candelilla wax, montan wax, and microcrystalline waxes, preferably beeswax.

12. The cosmetic composition according to one of the preceding points, wherein the composition includes, based on its total weight, 1.0 to 14% by weight, preferably 1.5 to 12% by weight, and in particular 2.0 to 10% by weight of an emulsifier.

13. The cosmetic composition according to one of the preceding points, wherein the emulsifier selected is from the group of anionic emulsifiers, preferably from the group of alkyl and/or alkenyl ether phosphate, in particular phosphoric acid mono-, di-, or triesters of alkoxylated C12/C14 fatty alcohols.

14. The cosmetic composition according to one of the preceding points, wherein the emulsifier is selected from the group of nonionic emulsifiers, preferably from the group of ethoxylated unsaturated fatty alcohols, in particular from the group of ethoxylated unsaturated C16-18 fatty alcohols with an average ethoxylation degree of 4 to 6.

15. The cosmetic composition according to one of the preceding points, wherein emulsifier f) is selected from mixtures of anionic and nonionic emulsifiers, preferably from mixtures of phosphoric acid mono-, di-, or triesters of alkoxylated C12/C14 fatty alcohols with ethoxylated unsaturated C16-18 fatty alcohols with an average ethoxylation degree of 4 to 6.

16. The cosmetic composition according to one of the preceding points, wherein the composition includes, based on its total weight, less than 2.5% by weight, preferably less than 2.0% by weight, and in particular less than 1.1% by weight of water.

17. The cosmetic composition according to one of the preceding points, wherein the composition, based on its total weight, consists of at least 60% by weight, preferably at least 70% by weight, and in particular at least 80% by weight of components a) to g).

18. Use of a cosmetic composition according to one of the preceding points for the temporary shaping of keratin-containing fibers, in particular human hair.

19. A method for the temporary shaping of keratin-containing fibers, in particular human hair, in which the keratinic fibers are acted upon by a cosmetic composition according to one of points 1 to 17 and are temporarily fixed in their shape.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition comprising, based on its total weight,
    a) 10 to 90% by weight of hydrocarbons with a melting point between 38° C. and 58° C.,
    b) 20 to 45% by weight of aluminosilicate,
    c) 0.01 to 7.0% by weight of a hydrophobized metal oxide powder, said hydrophobized metal oxide powder being a hydrophobized silicate obtained by silanization of pyrogenic silicon dioxide
    d) 0.01 to 3.0% by weight of at least one white pigment,
    e) 3.0 to 15% by weight of wax,
    f) 0.5 to 15% by weight of an emulsifier, and
    g) less than 3.0% by weight of water.

2. The cosmetic composition according to claim 1, wherein the composition includes, based on its total weight, 15 to 70% by weight of the hydrocarbon or hydrocarbon mixture with a melting point between 38° C. and 58° C.

3. The cosmetic composition according to claim 1, wherein the composition includes, based on its total weight, 20 to 50% by weight of the hydrocarbon or hydrocarbon mixture with a melting point between 38° C. and 58° C.

4. The cosmetic composition according to claim 1, wherein the composition includes, based on its total weight, 25 to 40% by weight of the hydrocarbon or hydrocarbon mixture with a melting point between 38° C. and 58° C.

5. The cosmetic composition according to claim 1, wherein the composition comprises 25 to 40% of aluminosilicate.

6. The cosmetic composition according to claim 1, wherein the composition includes kaolin as the silicate from the group of phyllosilicate and aluminosilicate.

7. The cosmetic composition according to claim 1, wherein the white pigment is selected from the group consisting of: titanium oxide, zinc oxide, zinc sulfide, lithopone, and aluminum starch octenylsuccinate.

8. The cosmetic composition according to claim 1, wherein the wax comprises 4.5 to 13.5% by weight based on the total weight of the cosmetic composition.

9. The cosmetic composition according to claim 1, wherein the wax comprises 6.0 to 12% by weight based on the total weight of the cosmetic composition.

10. The cosmetic composition according to claim 1, wherein the wax comprises 7.0 to 11% by weight based on the total weight of the cosmetic composition.

11. The cosmetic composition according to claim 1, wherein the emulsifier comprises 1.0 to 14% by weight, based on the total weight of the composition.

12. The cosmetic composition according to claim 1, wherein the emulsifier comprises 1.5 to 12% by weight, based on the total weight of the composition.

13. The cosmetic composition according to claim 1, wherein the emulsifier comprises 2.0 to 10% by weight, based on the total weight of the composition.

14. A method for the temporary shaping of keratin-containing fibers, comprising, in which the keratinic fibers are acted upon by a cosmetic composition according to one of claim 1 and are temporarily fixed in their shape.

* * * * *